United States Patent [19]
Beisang, III

[11] Patent Number: 5,087,248
[45] Date of Patent: Feb. 11, 1992

[54] DEVICE FOR ANCHORING AN INTRAVENOUS NEEDLE

[75] Inventor: Arthur A. Beisang, III, Shoreview, Minn.

[73] Assignee: Genetic Laboratories Wound Care, Inc., St. Paul, Minn.

[21] Appl. No.: 481,319

[22] Filed: Feb. 20, 1990

[51] Int. Cl.[5] ............................................. A61M 5/32
[52] U.S. Cl. ................................................. 604/180
[58] Field of Search ................ 604/177, 180, 307; 128/155

[56] References Cited

U.S. PATENT DOCUMENTS

| | | | |
|---|---|---|---|
| 1,052,274 | 2/1913 | Purdy | 604/307 |
| 3,683,911 | 8/1972 | McCormick | 604/180 |
| 3,782,377 | 1/1974 | Rychlik | 128/888 |
| 3,856,020 | 12/1974 | Kovac | 604/169 |
| 3,900,026 | 8/1975 | Wagner | 128/888 |
| 4,059,105 | 11/1977 | Cutruzzula | 604/180 |
| 4,235,234 | 11/1980 | Whitney et al. | 604/117 |
| 4,324,236 | 4/1982 | Gordon et al. | 604/177 |
| 4,346,700 | 8/1982 | Dunshee et al. | 128/155 |
| 4,380,234 | 4/1983 | Kamen | 604/180 |
| 4,460,356 | 7/1984 | Moseley | 604/180 |
| 4,490,141 | 12/1984 | Lacko et al. | 604/180 |
| 4,627,842 | 12/1986 | Katz | 604/177 |
| 4,704,177 | 11/1987 | Vaillancourt | 604/307 |
| 4,726,716 | 2/1988 | McGuire | 604/180 |
| 4,822,342 | 4/1989 | Brawner | 604/180 |
| 4,838,868 | 6/1989 | Forgar et al. | 604/180 |
| 4,863,432 | 9/1989 | Kvalo | 604/177 |

FOREIGN PATENT DOCUMENTS

| | | | |
|---|---|---|---|
| 0416655 | 9/1934 | United Kingdom | 604/307 |
| 2211417 | 7/1989 | United Kingdom | 604/180 |

Primary Examiner—C. Fred Rosenbaum
Assistant Examiner—Sharon Finkel
Attorney, Agent, or Firm—Haugen and Nikolai

[57] ABSTRACT

An adhesive patch for anchoring an intravenous needle to the skin of a patient at the transcutaneous insertion site is disclosed in which a patch of continuous flexible asymmetrically elastic sheet material having one side covered with a layer of biocompatible adhesive is provided substantially shaped as large and small abutting parallel rectangles integrally joined parallel to the easy axis of elasticity and adapted to engage an intravenous needle. The small rectangle is configured such that a portion can disengage from the larger rectangle and fold on itself as a tab and adhesively engage the periphery of the hub of the needle and wherein the larger rectangle has a central shaped cut out facing the small rectangle and is adapted to fold over the tab and adhesively attach to the skin thereby attaching the entire assembly to the skin. A layer of peelable release paper adhering to said adhesive is provided for packaging.

2 Claims, 2 Drawing Sheets

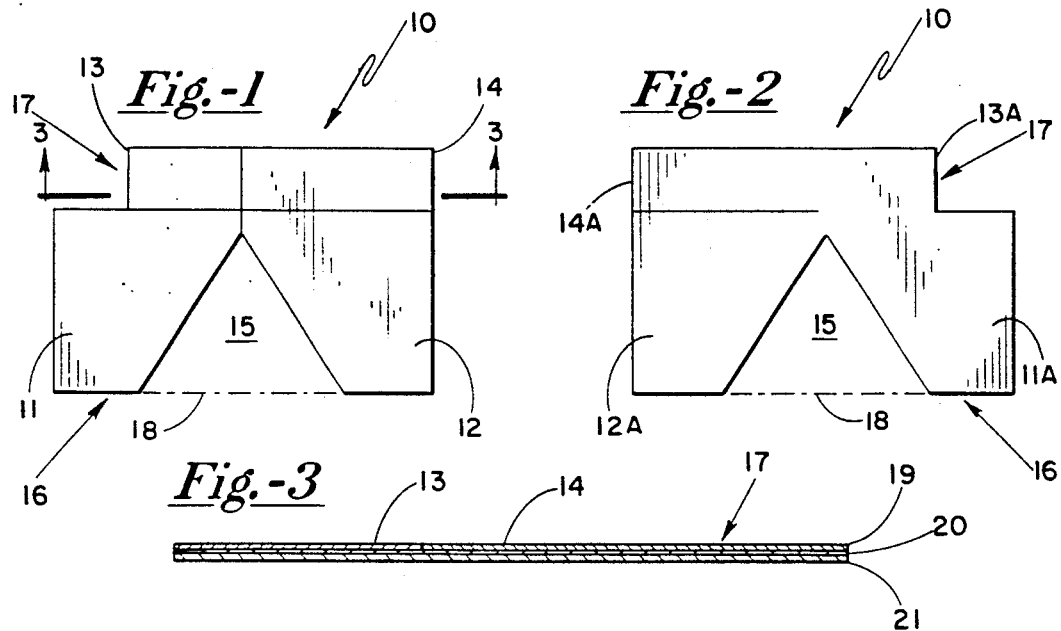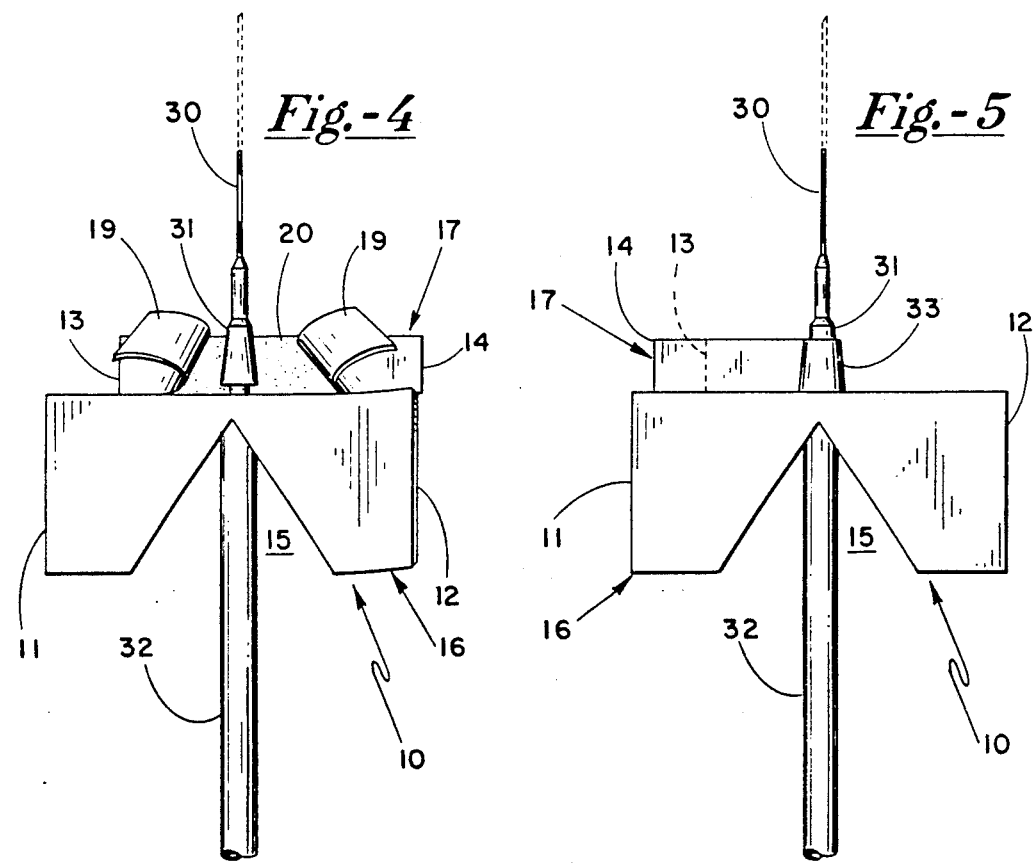

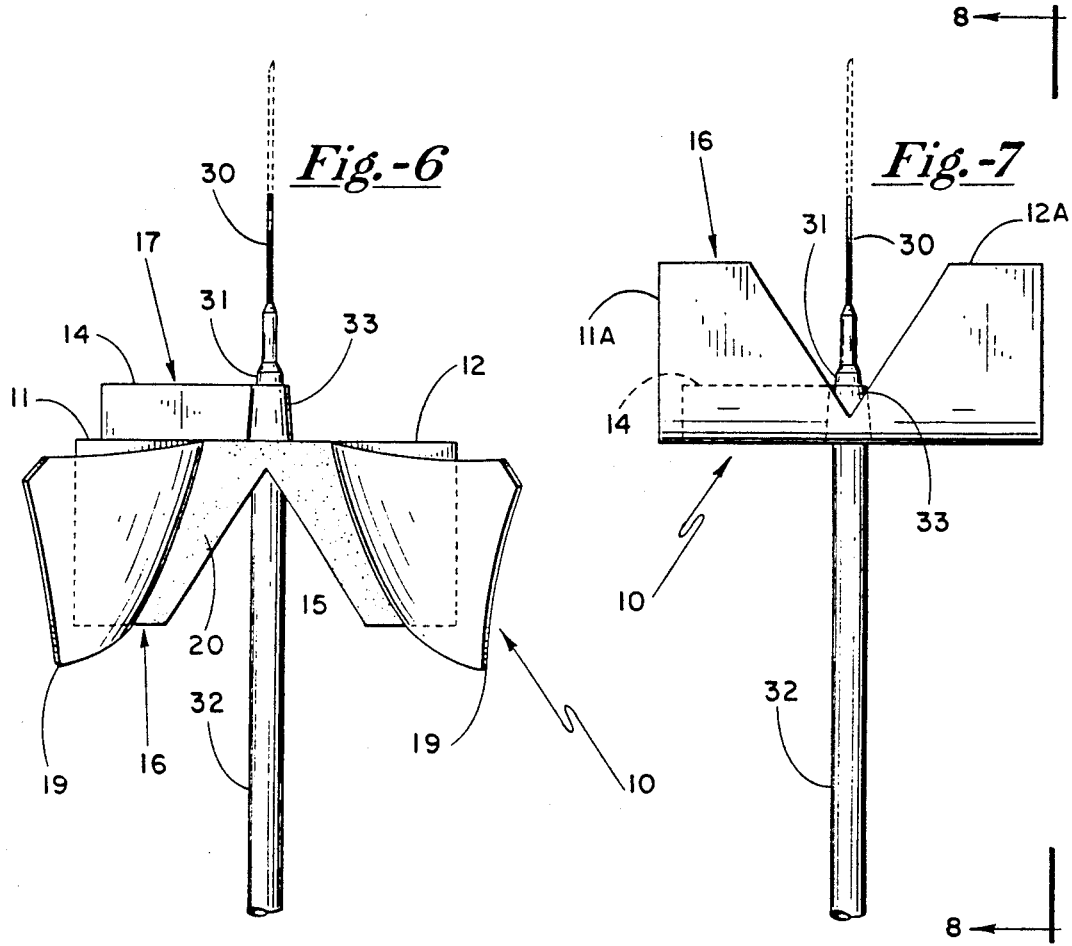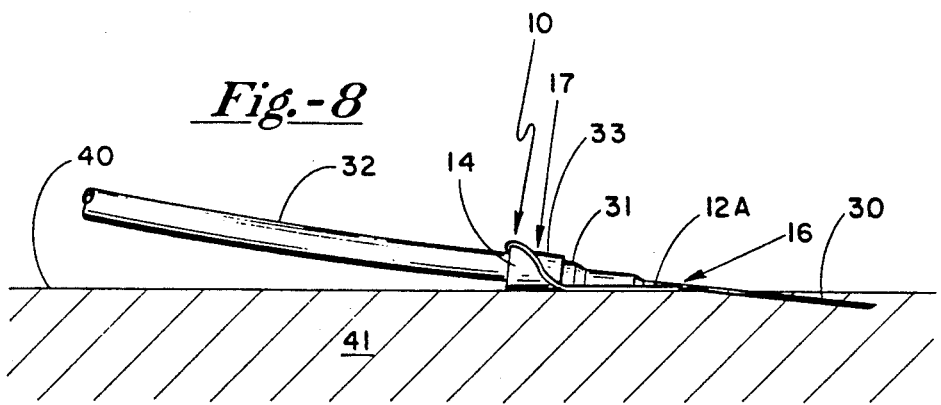

DEVICE FOR ANCHORING AN INTRAVENOUS NEEDLE

BACKGROUND OF THE INVENTION

I. Field of the Invention

The invention relates generally to a disposable adhesive device used for the purpose of securing a subcutaneously inserted intravenous (I.V.) needle in place at the skin and more particularly, to a prefabricated adhesive appliance especially shaped both to facilitate adherence to the hub of the intravenous needle and also to the skin surface to stabilize the position of the needle in relation to the skin, making dislodgement of the needle more difficult.

II. Discussion of the Related Art

In order to deliver intravenous medication and fluid to a patient, one must have vascular access for a period of time ranging from several hours to several days. Vascular access is achieved by introducing a hollow core needle transcutaneously into the lumen of a blood vessel. Normally, the needle is advanced through the skin until the hub of the needle is at the skin surface. If the needle is not sufficiently secured in place, the needle dislodges from the vessel quite easily, thereby requiring repeat of the painful insertion procedure, and possibly tissue damage or necrosis may also result.

In the past, one practice for immobilizing the hub of the needle at the skin interface has included the use of adhesive tape strips criss-crossed about the hub and positioned onto the skin. The number of strips of tape and the manner of application is left to the best judgment of the medical attendant. Yet another commonly used method of attachment has been to place an adhesive backed patch of material over the needle hub and skin. Another method of securing the needle hub to the skin includes laying a patch of adhesive material over the skin and the needle. This method is unstable with respect to the needle orientation and makes the positioned needle subject to easy dislodging from the vein, and increases the likelihood of the needle pulling out of the skin. An additional consideration is that the adhesive is only in contact with a small portion of the needle hub so that there is little resistance to prevent the hub from rotating around its axis. If the hub and the flexible needle are not in alignment, a torsional force on the needle will result which may cause the needle to be dislodged from the blood vessel lumen.

More recently, more sophisticated devices have become available for establishing a subcutaneous angle of an intravenous needle and the securing of the needle in place. One such device is illustrated and described in U.S. Pat. No. 4,627,842 which includes an assembly in which the needle is mounted transversely of the central section of an elongated, flexible, foldable body in which a tapered foam pad having a pressure sensitive adhesive is used to establish the correct needle angle and also position the assembly on the skin of the recipient. In this and other such assemblies, a great deal of attention is paid to supporting and positioning the needle with relative respect to the subcutaneous administration of medication; however, the problem of stabilizing the fixed position of the needle with respect to the skin receives very little consideration. Thus, dislodging of the needle by patient movement or other external causes remains a serious problem with these devices as well as with the customary use of adhesive tape or bandage materials alone. Approaches which have achieved good, repeatable needle placement have a lacked stability with respect to adhesion to the skin; and those approaches which have addressed the problem of adhesion to the skin have been found lacking with respect to securing the needle properly in relation to the lumen of the blood vessel of interest.

SUMMARY OF THE INVENTION

The present invention provides a preformed intravenous needle anchoring device which can be applied in only a few seconds and which can be left in place for prolonged periods of time without causing irritation to the skin. The anchor securely holds the hub of a needle to prevent dislodgement and provides improved adhesion to the skin to better resist movement of the needle out of the skin. The invention further provides a barrier to infection by covering the point of the needle insertion while being able to monitor the site for infection and signs of fluid infiltrations into the proximate tissues. The invention enables an intravenous needle to be securely anchored in place using an anchor which is neat in appearance and effective in use.

The present invention provides a prefabricated adhesive assembly patch which addresses both fixing needle position and comfortable skin adhesion. The assembly is preshaped to facilitate attachment of the needle hub to the skin surface. In the present invention the skin interface material is preferably a thin plastic backing material of a type exhibiting asymmetric or uniaxial stretch properties, permeable to moisture and air which exhibits a compliance modulus irrespective of thickness in the range of 0.5 to 110 pounds per inch, along with an elastic recovery which is less than about 98%. Examples of such material include woven and nonwoven polymers, i.e., polyurethane, polyethylene, polyamides. However, any thin, preferably clear, plastic material of a class which exhibits air and moisture permeability and can be caused to properly adhere to skin during use and thereafter can be atraumatically removed can be used.

The anchoring device of the present invention is preferably fabricated from a single section of material shaped to have an intravenous hub engaging zone integrally joined to a skin engaging zone. The easy stretch axis of the asymmetrically or uniaxially stretching pad material, if such is used, is preferably aligned so that it is perpendicular to the axis of the needle. The hub engaging portion of the device is preferably generally rectangular in shape with the easy stretch axis running parallel to the longer dimension of the rectangle. The hub section has a portion of one side of the longer dimension continuous with the skin engaging zone. The skin engaging zone may also be generally rectangular in shape with the easy stretch axis aligned with the longer dimension of the rectangle. The dimensions of the skin engaging portion are generally larger than the hub engaging portion to achieve additional overlay mounting stability. A shaped defect or cut out, which may be generally triangular, may be provided in the center portion of the skin engaging portion, on the side opposite the hub engaging section. The apex of the triangular or other recess is disposed to point toward the hub engaging portion and is located at the midpoint of the long side. The use of the defect will become apparent in regard to the application of the device. The adhesive portions of the invention are covered by a release paper material in a well-known manner prior to use and the entire device sealed in an aseptic environment.

In use, after the I.V. needle has been inserted, the device is removed from its sterile packaging. Portions of the release paper covering the hub engaging zone are peeled back. The device is positioned with the exposed adhesive side facing away from the skin, and the needle engaging portion positioned on the opposite side of the hub from the needle. The hub engaging section of the device is then positioned under the needle hub with the adhesive side facing the hub away from the skin. The hub engaging flap is then wrapped completely around the hub with any excess self-adhering and/or attaching to the skin. The release paper is then completely removed from the skin engaging portion with the adhesive side still facing away from the skin. The skin engaging portion is then folded over the needle hub including the hub engaging flap, and affixed to the skin on the sides of the hub covering the hub engaging flap and affixed to the skin overlying the needle.

The uniaxial stretch properties of the preferred backing material allow the anchoring device to exhibit "dynamic adhesion", meaning that it has stretch properties similar to that of skin and can move with the movement of the skin sideways and yet resist movement of the needle in and out of the skin. In addition, the design provides for 360° adherence of the anchor about the hub of the needle, allowing for more secure fastening and resulting in better resistance to needle dislodgement. The triangular cutout provides for better visualization of the skin when one is looking for infection or infiltration as does the use of transparent materials of construction in an embodiment without the cut out, as the site of needle entry can be viewed with the device in place. The alternative embodiment (without cut out) has the added advantage of forming a barrier to infection at the site of needle insertion. This embodiment is preferred when transparent materials are used.

BRIEF DESCRIPTION OF THE DRAWINGS

In the drawings:

FIG. 1 is a top view of the needle anchoring device of the invention as removed from a package;

FIG. 2 is a bottom or reverse view of the device of FIG. 1;

FIG. 3 is a side elevation view showing the layers of the device of FIG. 1;

FIG. 4 is a view of the anchoring device of the invention first slipped under the hub of an I.V. needle with release paper partially peeled back illustrating the first step of application;

FIG. 5 is a view similar to FIG. 3 showing the second step of application;

FIG. 6 is a view similar to FIG. 3 showing the third step of application;

FIG. 7 is a top view of a completely applied I.V. anchoring device in accordance with the invention; and FIG. 8 is a transcutaneous elevational view, partially in section, showing the I.V. needle anchored in place.

DESCRIPTION OF THE ILLUSTRATIVE EMBODIMENT

FIG. 1 depicts a typical top view of an anchoring device in accordance with the present invention as it might be removed from an aseptic package divided into portions as at 11, 12, 13, and 14 which also denote release paper sections. The bottom, as shown in FIG. 2, is plain and divided only between 14A and 12A. The sections are noted by 11A, 12A, 13A and 14A for convenience. As can readily be seen, the device has a generally rectangular shape and may or may not be provided with a cut out or defect 15. Line 18 indicates that a solid rectangular embodiment may be used. The device is generally divided into a skin engaging portion in the form of the large rectangular section 16 which includes the portions 11 and 12 together with the cut out portion 15 which may be triangular and, a needle hub engaging section 17 which includes the flap portion 13 and portion 14 which together engage the hub of the I.V. needle.

The preferred material of the device is a polymeric material having an asymmetric elasticity. This quality can be given to many plastic materials during processing and normally occurs when a polymeric material has a pattern of woven or non-woven fibers having a generally oriented so as to exhibit a preferred or easy direction of stretch which one skilled in the art can take advantage of in positioning and cutting sections made from such material. The preferred easy direction of stretch is generally along a direction perpendicular to the axis of the I.V. needle (FIGS. 4-8) FIG. 1 by the arrow 18.

FIG. 3 depicts the layered structure of needle anchoring device of FIG. 1 as received including release paper 19, adhesive material 20 which covers the entire elastic pad layer 21. To facilitate application of the needle anchor in accordance with present invention, the release paper layer is preferably segmented into four parts corresponding to the sections 11-14 designated in FIG. 1. These, of course, serve to protect the integrity of the adhesive prior to use and facilitate application of the device.

FIGS. 4-7 illustrate the steps of a typical application of the intravenous needle anchoring device of the invention. In FIG. 4, the intravenous needle 30 has been inserted subcutaneously and the anchoring device of the invention has been slid into position with the smaller rectangular section underneath the inserted needle to a point where sections 13 and 14 addresses the needle hub 31. The release paper or backing material 19 is shown partially removed from the sections 13 and 1 exposing the needle hub 31 to the adhesive material beneath the release paper. The remainder of the I.V. needle assembly is shown at 32 and can be attached to a tube or other fluid administering device (not shown) in a well-known manner.

In FIG. 5, the tab section 14 has been folded over the needle hub 31 at 33 thereby surrounding the needle hub 31 with the adhesive side of the tabs 13 and 14 and fixing the needle hub to the anchoring device and the skin. At this point, the portions 11 and 12 still have their backing material on and this is shown peeled back in the illustration of FIG. 6. After removal of the backing material or release paper from sections 11 and 12, the skin engaging section is simply folded forward over the hub engaging portion and pressed onto the skin such that the entire device is firmly, adhesively attached to the skin with the needle properly positioned as shown in FIG. 7. It should be noted that the needle hub 31 then is engaged throughout 360° of its periphery by the hub flap which is then firmly positioned with regard to the skin engaging by the overlying skin portions 11 and 12. It may further be noted that the defect or removed section 15, upon application, is situated or disposed so that the skin directly above the needle insertion site can be observed for signs of infection, I.V. infiltration or other possible problems.

FIG. 8 depicts another view of the inserted, anchored intravenous needle showing the anchoring device of the invention in place. The skin is denoted by 40 and the subcutaneous area by 41.

With respect to the plastic material which makes up the intravenous anchoring device of the invention, it should be one that is pervious to moisture and air which allows the area beneath it to respire as normally as possible after it is applied to the skin. This is especially important when quantities of intravenous liquid are administered to a patient over long periods of time through the same needle.

As mentioned above, the material is normally fabricated from large sheets of such material and, for example, a rotary die cutting operation. In this manner, it is possible to cut the material at a predetermined angle with respect to the easy stretch axis thereby yielding a product with the desired compliance modulus and desired elastic recovery. The closer the plastic material comes to reflecting the properties of the skin to which it is attached, the better the anchor of the needle achieved. It has been found that a compliance modulus irrespective of thickness in the range of from 0.5 to 110 pounds per inch and an elastic recovery factor somewhat less than 98% yields excellent results and a product which has been found to exhibit stretch characteristics correspondingly close to that of skin. In this manner, once attached to the skin, the anchoring device will flex with skin movement to thereby avoid puckering and disattachment of the anchoring device during movement of the patient's arm or other extremity to which such devices are normally attached.

The adhesive material must be a bio-compatible, non-allergenic material which can adhere to the skin over long periods of time yet later release from the skin atraumatically. Examples of materials which have been successfully used include polymethacrylate, polyvinyl ethyl ether, polyacrylate and acrylic ether copolymer. These adhesives have found wide spread use in the past in various forms of bandages and wound dressings and exhibit good adhesion properties even to so-called non-stick surfaces such as silicone plastics and hydrophilic coatings. In addition, they are substantially non-irritating to dermal tissues. The release paper used is one which is compatible with the particular adhesive material utilized. Various types of such release papers are known in the art and are available for each of the adhesives.

What is claimed is:

1. A stabilizing foldover adhesive anchoring device for securing an intravenous needle to the skin of a patient at a point spaced from the transcutaneous insertion site by engaging the hub of the needle comprising:

a continuous patch of flexible asymmetrically elastic sheet material having an easy axis and a hard axis with regard to the elasticity;

wherein the patch is substantially rectangularly shaped and divided to include large and small abutting parallel rectangular sections integrally joined for a distance parallel to the easy axis of elasticity and adapted to engage an intravenous needle disposed generally at right angles to the easy axis of the material;

the small section further being configured with a tab portion that is predisposed to readily disengage in part from the larger section and fold on itself to adhesively engage the periphery of the needle hub therebetween;

wherein the large section has a central substantially triangularly shaped cut-out facing the small section and is adapted to fold over itself and the flap portion containing the hub and adhesively attach to the flap portion and the skin, thereby attaching the entire assembly to the skin with the out-out exposing the transcutaneous insertion site; and an amount of adhesive material applied to one surface only of the patch material such that the patch is required to be positioned with the adhesive side away from the skin prior to engaging the needle.

2. A method of securing an intravenous needle to the skin of a patient utilizing a flexible elastic sheet anchoring device having adhesive applied on one side only to secure the needle hub comprising the steps of:

providing a patch of flexible elastic sheet material of a predetermined shape and size and having a quantity of adhesive material applied to one surface only thereof wherein the sheet of flexible elastic material is further functionally divided into a needle hub engaging portion and a skin attaching portion, the needle hub engaging portion further comprising a partially separated fold over flap capable of folding on itself and adhesively engaging the periphery of the hub of the needle therebetween, a portion of the flap remaining integral with the skin attaching portion of the patch;

placing the patch under the needle with the adhesive side up, the hub engaging portion beneath the hub and the skin engaging portion extending back along the needle axis toward the proximal end thereof;

causing the fold over flap to fold and peripherally engage the hub and itself; and folding the skin attaching portion on itself over the previously folded needle engaging flap portion adhesively attaching it to both the needle engaging flap and to the skin, thereby attaching the entire assembly to the skin.

* * * * *

UNITED STATES PATENT AND TRADEMARK OFFICE
CERTIFICATE OF CORRECTION

PATENT NO. : 5,087,248
DATED : February 11, 1992
INVENTOR(S) : Arthur A. Beisang, III It is certified that error appears in the above-identified patent and that said Letters Patent is hereby corrected as shown below:

In column 6, line 21, delete "out-out" and insert -- cut-out -- .

Signed and Sealed this

Eighth Day of June, 1993

Attest:

MICHAEL K. KIRK

*Attesting Officer*     *Acting Commissioner of Patents and Trademarks*